United States Patent [19]

Takayanagi

[11] Patent Number: 4,956,457
[45] Date of Patent: Sep. 11, 1990

[54] DISAZO DISULFONAMIDES COMPOUNDS

[76] Inventor: Takeo Takayanagi, 41 Ellsworth Ave., Yonkers, N.Y. 10705

[21] Appl. No.: 391,945

[22] Filed: Aug. 10, 1989

Related U.S. Application Data

[62] Division of Ser. No. 876,834, May 20, 1986, Pat. No. 4,863,910.

[51] Int. Cl.$^5$ ............... C07C 107/00; C07C 107/04; C07C 107/06; C07C 107/08
[52] U.S. Cl. .................... 534/643; 534/797; 534/827; 534/832; 534/646; 534/829; 534/716
[58] Field of Search ............... 514/150; 534/643, 827, 534/832, 797

[56] References Cited

U.S. PATENT DOCUMENTS

| | | | |
|---|---|---|---|
| 2,243,617 | 5/1941 | Bonhote et al. | 534/827 |
| 3,546,202 | 12/1970 | Budesinsky et al. | 534/827 X |
| 4,145,299 | 3/1979 | Ford et al. | 534/827 X |

FOREIGN PATENT DOCUMENTS

| | | | |
|---|---|---|---|
| 2703492 | 8/1978 | Fed. Rep. of Germany | 514/150 |
| 55-45607 | 3/1980 | Japan | 514/150 |
| 55-45608 | 3/1980 | Japan | 514/150 |
| 55-145699 | 11/1980 | Japan | 514/150 |
| 56-32472 | 4/1981 | Japan | 514/150 |

Primary Examiner—Floyd D. Higel
Attorney, Agent, or Firm—Bierman and Muserlian

[57] ABSTRACT

The new azo compounds are represented by the following general formula I

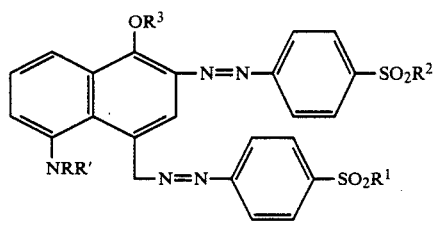

Wherein R and $R^1$ are hydrogen, —COCR$_3^4$—COCHR$_2^4$, —SO$_2$CH$_3$, —CO$_2$C$_2$H$_5$, —CH$_2$CH$_2$R$^4$, —(CH$_2$CH$_2$R$^4$)$_2$, —CH$_2$CH$_2$OH, —CONHCH$_2$CH$_2$R$^4$ or —CH$_2$CH$_2$OCONH$_2$ and $R^4$ is Cl or a group of the formula

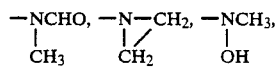

—NHCO$_2$CH$_3$CH$_2$OH, —NHCO$_2$C$_2$H$_5$, —NHOH, —NHCONHOH, or —NHCH$_3$, whereby $R^1$ and $R^2$ are similar or dissimilar.

2 Claims, No Drawings

DISAZO DISULFONAMIDES COMPOUNDS

PRIOR APPLICATION

This application is a division of U.S. patent application Ser. No. 876,834 filed May 20, 1986, now U.S. Pat. No. 4,863,910 issued Sept. 5, 1989.

This invention relates to the new azo compounds, their azo complex compounds, together with process for producing the same, and more particularly is concerned with producing pharmaceutical preparation containing the same as effective ingredient.

The new azo compounds are represented by the following general formula I

Wherein
R and R' are hydrogen, $-COCR_3^4-COCHR_2^4$, $-SO_2CH_3$, $-CO_2C_2H_5$, $-CH_2CH_2R^4$, $-(CH_2CH_2R^4)_2$, $-CH_2CH_2OH$, $-CONHCH_2CH_2R^4$ or $-CH_2CH_2OCONH_2$ and $R^4$ is Cl or a group of the formula $-NCHO$, $-N-CH_2$, $-NCH_3$,
|         |/        |
$CH_3$    $CH_2$    $OH$ $-NHCO_2CH_3CH_2OH$  $-NHCO_2C_2H_5$, $-NHOH$, $-NHCONHOH$ or $NHCH_3$. whereby R and R' are similar or disimilar.

$R^1$ und $R^2$ are $-NHCH_2CH_2Cl$, $-NHCONHOH$, $NHCO_2C_2H_5$, 6-mercaptpurinyl, 5-fluoruracilyl, sulfisomidyl or prednisolyl. whereby $R^1$ and $R^2$ are similar or dissimilar.

$R^3$ is hydrogen, $-COCHR_2^4$, $-COCR_3^4$, $-SO_2CH_3$, $-COC_2H_5$ $-CH_2CH_2R^4$ or $-CONH_2$. And $R^4$ has the meaning above mentioned, whereby R and $R^3$ are similar or dissimilar.

The new azo compounds form its salts, especially metal salts, and they are employed in the producing of complex-compounds. The azo compound of formula I, its salt especially metal salts can be easily form the complex-compound with the following selected compounds, for example, antitumor agents:
  cyclophosphadmide, thiotepa, 6-mercaptopurine, vinblastine, 6-mercaptopurine, 5-fluoruracil, L-asparaginase, nitromine or prednisolone.
antibiotica: chloramphenicol, streptomycin or penicillin. curative organic dyestuff:
  pyoktanin, methylene blue or acriflavin.
organic compounds having therapeutic effect:
  abscisinic acid, p-hyroxybenzoic acid, maleic acid, D-glucosaminehydrochloride, glucoside.

The compounds of the formula I can be not only coagulated with 1 component above mentioned, but it can be also coagulated with several components at a time, which are similar or various groups of action.

The condensation of the compounds having the formula I were carried out smoothly in coherent medium under dropping of selected metal salts solution.

Hereby employed metal salts were selected out of many metals according to the purpose.

The new complex compounds of this invention have accurate inhibitory properties against the growth of tissue; therefore, the complex are available for treatment of malignant tumor or new formation even mycosis etc. In consequence of their macromolecular constitution, the complex compounds are well tolerable against human body and shows no side effect. Furthermore all the complex compounds are easily soluble in water or in saline solution, consequently, it is convenient to the clinical use.

Furthermore, it is now substantiated that this invention has the advantage of obtaining many effective substances through adequate variation and combination of the substituents and the condensation components.

Finally, it has been founded numerous new effective compounds necessary for combination therapy in the treatment of malignant disease.

The compounds of this invention are, as above mentioned nearly non toxic, tasteless or no sideseffect, may be per os taken with good tolerance. Therefore they are suitable for preparing pharmaceutical composition, which are an object of this invention.

According to this invention the manufacturing of the compounds having following formula III.

wherein R, R' and $R^3$ have the meaning above mentioned, were coupled with (a) 2 mole of diazosulfonamide-component having the formula IVa or (b) with 1 mole of component IVa, IVb each one after an other

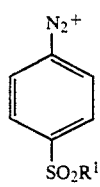
IVa

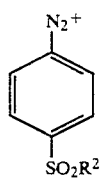
IVb

Whereby R¹ and R² are dismimilar and have the meaning above mentioned.

The compounds thus obtained can be employed in the preparation of complex-compounds with 5-Fluoruracil, Cyclophosphamide, 6-Mercaptopurin, P yoktanin, Prednisolon, Methylenblue, Vinblastin, Abcisinic acid, Maleic acid, or L-Asparaginase.

The azo coupling reaction of the compounds of formula III is smoothly effected in the well-known manner upon cooling. Hereby I have founded that the most suitable diazo-component for this reaction is ultimately aromatic diazonium group having sulfonamide group indicating in formula IV.

The preparing of chemotherapeutic effective azo-complex-compounds is accomplished in a solvent, particularly in ethylene glycol monoethyl ether, which is characteristically coherent and causes condensation and more over dissolves the compounds above mentioned.

The starting compounds of formula III will be prepared in the well-known manner from 5-amino-1-naphthol (II),

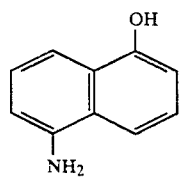

In case of acetylation of 5-amino-1-naphthol 1 mole or 2 equimolecular quantities of acid chloride was substituted at 10° C. When used equimolecular dichloro or trichloroacetyl chloride, then obtained the compounds having following formula Va and Vb.

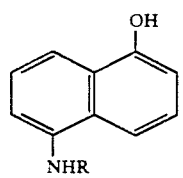

R = —COCHCl₂  Va

—COC Cl₃  Vb

When 2 mole acid chloride applied and by heating 160–180 C. if needed, catalyst was added then obtained the substance of following formula

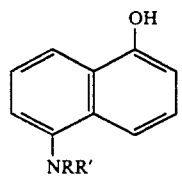
IVa

R, R = —COCHCl₂  Vc

—COC Cl₃  Vd

Instead of acid chlorides, similar acid chloride anhydride or isocyanate are employed.

In substitution of 5-amino-1-naphthol(II) with equimolar quantity of 2-chloroethylisocyanat, then obtained the compounds of the following formula

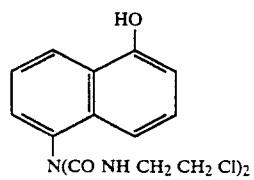
Ve

The substitution of 5-amino-1-naphthol (II) with ethylen oxide is carried out in dioxane solution by adding small quantity of water. The obtained compound has the following formula

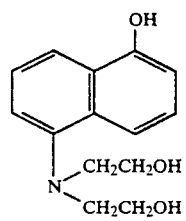
VI

Instead of ethylene oxide can be used hereby another adequate alkylenoxide.

If the amino group of starting substance 5-amino-1-naphthol was already substituted, there can be substituted with calcium cyanate in the presence of hydrochloric acid. The effected compound is as follows.

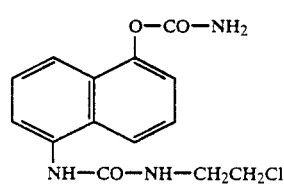
VII

From the compounds of formula III, V–VII are obtained the compounds of the general formula I by coupling with 2 mole diazo-component of sulfonamide IVa, IVb mentioned above.

The coupled double sulfonamide groups play an important role according to the condensation, especially to the effectiveness, action or reaction of the complex-compounds.

If substitute hydrogen combined with nitrogen by Na, obtained the following formula:

—SO₂(Na)NR¹

—SO₂(Na)Nr²

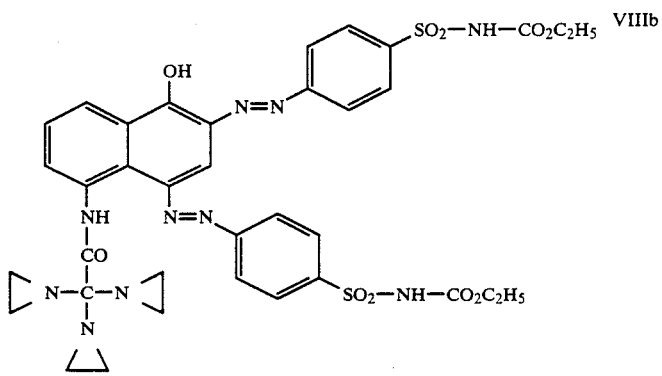

VIIIb

If substitute with Magnesium obtained following formula

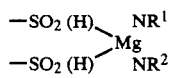

Whereby R¹ and R² are similar or dissimilar.

The following examples will serve to more specifically illustrate preparations according to this invention, as well well as the method of making them.

EXAMPLE 1

1.6 grams of 5-amino-1-naphthol were dissolved in 50 ml pyridine. To the solution there was added drop by drop 1 mole of trichloroacetylchloride upon cooling at 10° C. or below. The reaction mixture was over night on standing. Then it was poured into ice and the effected mass was in a small quantity of ethanol dissolved.

The mixture was heated in a pressure bottle for 2 hours at 130 C., adding a slight excess of methylformamides. After the substitution completed there was the solution After the substitution completed there was the solution poured into the diazosulfoethylurethane solution of 2 mole under cooling. Continuously were 5 grams of sodium acetate dissolved in water added into the mixture. After standing over night was the voluminous precipitate filtraed. The effected substance is dark almost black colored powder, which in water or alcohol insoluble and having following formula

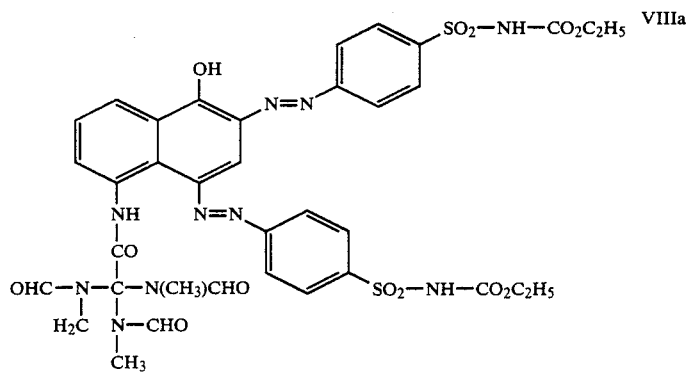

VIIIa

The intermediate products in the stoppered bottle were substituted with ethylenimine and worked up in analogous manner, then obtained dark almost black powder which was insoluble in water and in alcohol having following formula The compound above obtained of the formula VIIIa and equimolar quantities of methylviolet(pyoktanin) were dissolved in ethylene glycol monomethyl ether. Into this mixture was added dropwise 20% magnesium sulfate solusion until the solution changed to paste finally coagulated, indicating the condensation is completed. Hereupon, the reaction mixture is washed with benzene removing the presented solvent and dried up. The condensation product so obtained is readily soluble in water and in alcohol and it decomposes at over 200 C. under carbonizing having the following constitutions formula

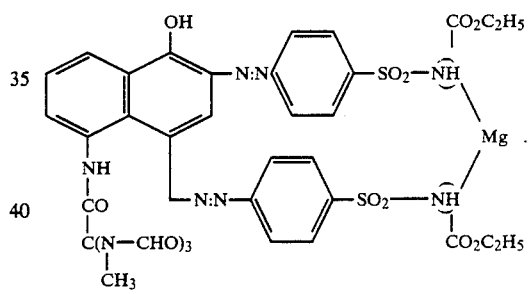

-continued

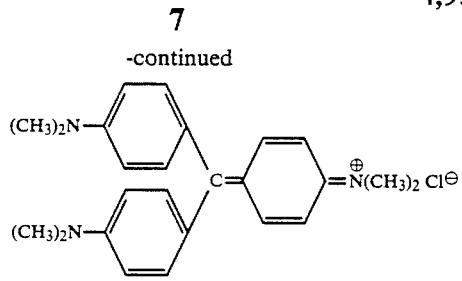

EXAMPLE 2

1.6 grams of 5-amino-1-naphthol was substituted in benzene under addition of 5 ml 2-chlor ethylisocyanate, whereby obtained the compound of the formula

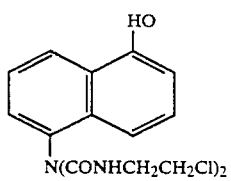   X

The product is isolated and the substance is mixed with about 6 grams of potassium cyanate. To this mixture is added hydrochloric acid dropwise until the foam forming stops. After standing over night it was treated with water, then resulted precipitate was filtrated and dried up. The product obtained above has following formula

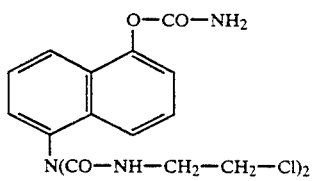   XI

The resulted mass was dissolved in 150 ml ethanol. The solution was added into the solution of in the well-known manner prepared 2 mole of diazosulfacytosine solution under cooling and finally was added into this solution 5 grams of sodium acetate dissolved in water. The effected voluminous precipitate was filtrated. The new product has the following formula

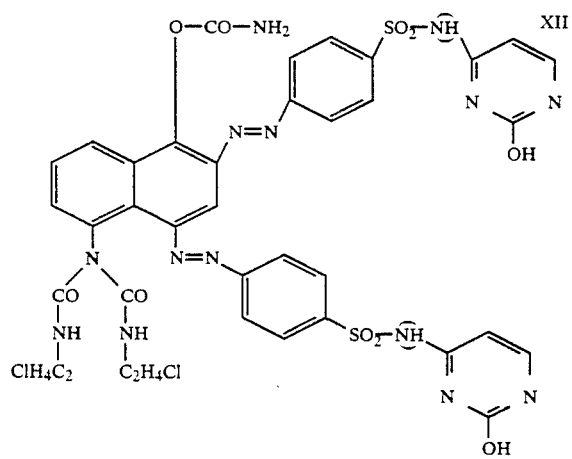   XII

The resulted substance was in adequate quantities of ethylene glycol monomethyl ether dissolved. Into the solution was added equimolecular quantities of pyoktanin successively was sodium hydroxide solution dropwise added until the solution turns purple colored. At this point is the condensation completed.

The substance will be isolated as a dark powder which is readily soluble in water. The compound is decomposed at 200° C. and has the following constitution formula

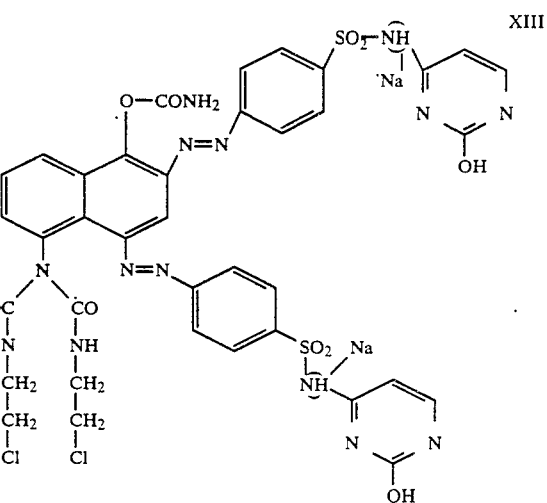   XIII

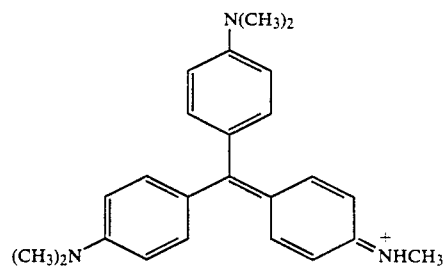

EXAMPLE 3

A mixture of 3 grams of 5-amino-1-naphthol, 20 ml dioxane, 6 ml distilled water and 6 grams of ethylenoxide were in a pressure bottle 2 h long at 30° C.–40° C. heated, there can be obtained the product of following formula

   XIV

The substance obtained above was in small quantities of ethanol dissolved, and was added upon cooling into the solution of in the well-known manner prepared, 2 mole of diazosulfomethylaminesolution upon cooling. Finally, 5 grams of sodium acetate dissolved in water were added into the solution. The effected voluminous precipitate was filtrated. The product has the following constitution formula

XV

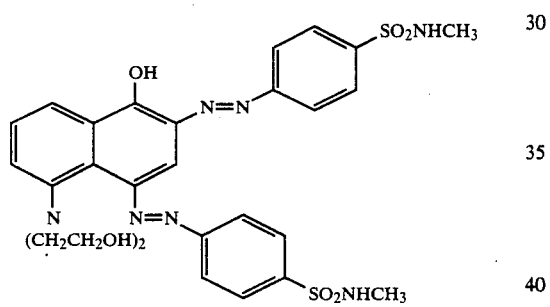

The resulted substance was dissolved in 50 ml benzene by adding 2-3 ml pyridine. Into the reaction mixture were added 10 ml thionyl chloride drop by drop. The substitution will be completed after 2 h heating. The resulted substance has the following formula

XVI

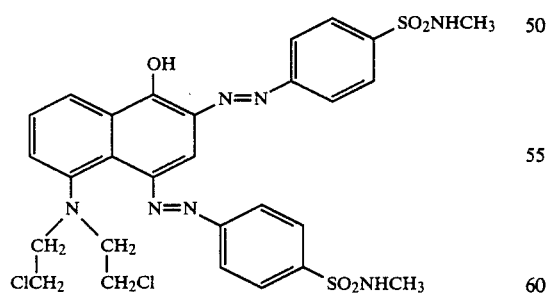

The resulted substance was dissolved in a adequate quantities of ethylene glycol monomethyl ether and to the solution added equimolecular quantities of prednisolone. Hereupon, to the solution was added copper sulfate solution drop by drop until the solution initially formed quickly congeals to a paste which is immediately turns coaglate. After washing and removal of solvent with benene, the resulted compound was dried up.

The product is readily soluble in water and azure colored powder having the following formula

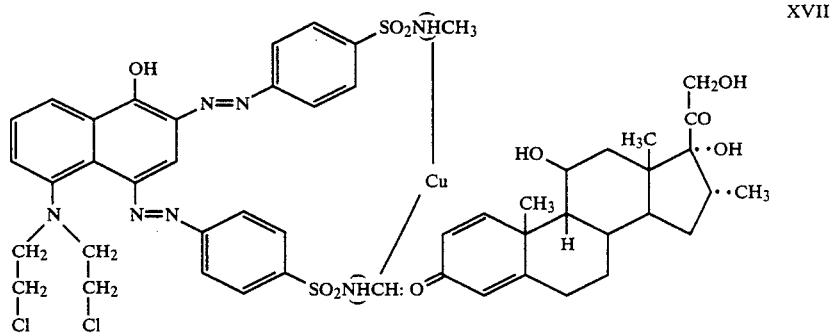

XVII

EXAMPLE 4

1.6 grams of 5-amino-1-naphthol was substituted in benzene with 5 ml 2-chloroethylisocyanate, whereby obtained the compound of the formula

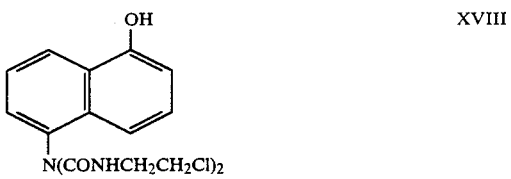

XVIII

The effected product was isolated and the substance is mixed with 5 grams of potassium cyanate and to this mixture was added hydrochloric acid solution drop by drop. Finally stopped the foaming and standing over night. The reaction mixture was treated with water and isolated the product having the following formula

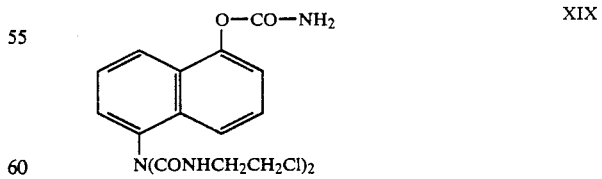

XIX

The resulted mass was dissolved in small quantities of ethanol. The solution there was added into the 2 mole quantities of dazosulfisomidine solution upon cooling. Continuously, into the mixture was added 5 grams of sodium acetate dissolved in water.

The effected voluminous precipitate was filtrated. The product has the following constitution formula

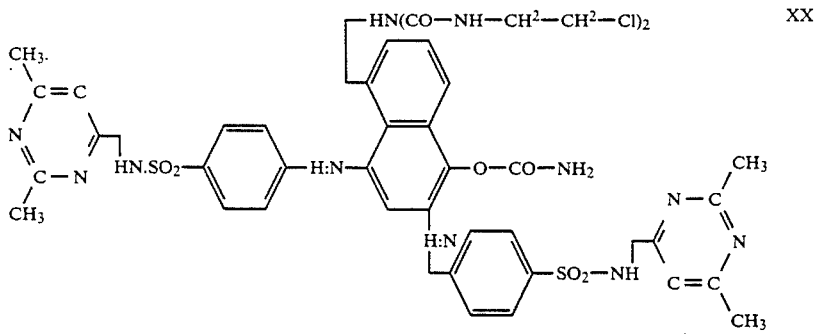

The compounds above mentioned having formula XX and equimolecular quantities of methyl violet, abscisinic acid or prednisolone were dissolved in a adequate quantity of ethylene glycol monomethyl ether.

Hereupon, into the mixture were $MgSO_4$ solution dropping-wise added until the mixture changed to paste and quickly coaglated. At this point is the condensation completed. The condensation product so obtained is easily soluble in water and alcohol and it decomposes at over 200° C. under carbonizing. The constitution formula of the product as follows:

I claim:
1. An azo compound of the formula

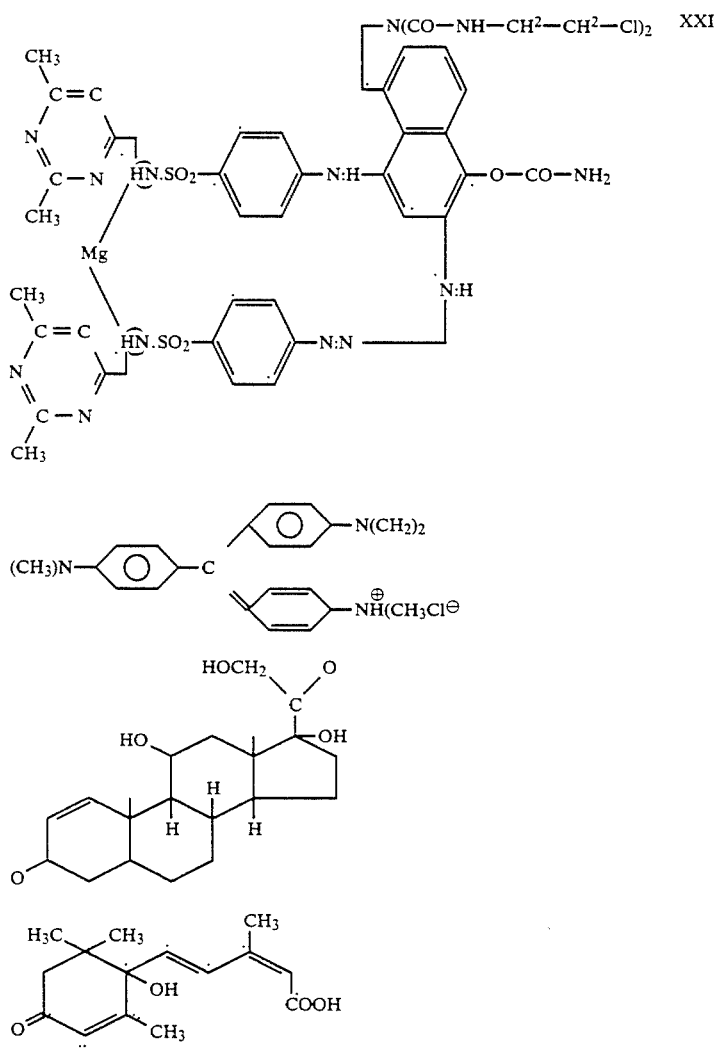

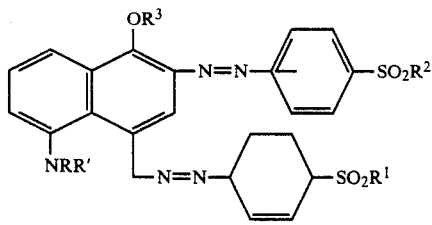

wherein R and R' are selected from the group consisting of hydrogen, —COCR$_3^4$, —COCHR$_2^4$, —SO$_2$CH$_3$, —CO$_2$C$_2$H$_5$, —CH$_2$CH$_2$R$^4$, —(CH$_2$CH$_2$R$^4$)$_2$, —CH$_2$CH$_2$OH, —CONHCH$_2$CH$_2$R$^4$ and —CH$_2$CH$_2$OCONH$_2$, R$^4$ is selected from the group consisting of chlorine,

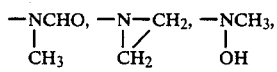

—NHCO$_2$CH$_2$CH$_2$OH, —HNCO$_2$C$_2$H$_5$, —NHOH, —NHCONHOH and —NHCH$_3$; R$^1$ and R$^2$ are individually selected from the group consisting of

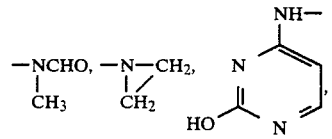

—NHCH$_2$CH$_2$Cl, —NHCONHOH, —NHCO$_2$C$_2$H$_5$, 6-mercapropurin, 5-fluoruracil and prenissolin, R$^3$ is selected from the group consisting of hydrogen, —COCHR$_2^4$, —SO$_2$CH$_3$, —COC$_2$H$_5$, —CH$_2$CH$_2$R$_4$ and —CONH$_2$, R$^4$ is the same as defined hereinabove or their salts.

2. An azo compound of claim 1 of the formula

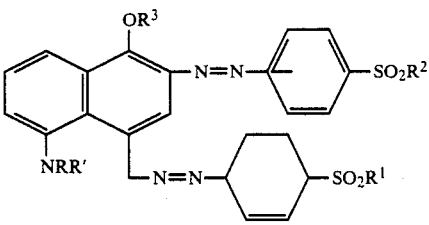

wherein R and R' are selected from the group consisting of hydrogen, —COCR$_3$, —COCHR$_2$, —SO$_2$CH$_3$, —CO$_2$C$_2$H$_5$, —CH$_2$CH$_2$R$^4$, —(CH$_2$CH$_2$R$^4$)$_2$, —CH$_2$CH$_2$OH, —CONHCH$_2$CH$_2$R$^4$ and —CH$_2$CH$_2$OCONH$_2$, R$^4$ is selected from the group consisting of Cl,

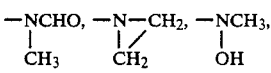

—NHCO$_2$CH$_2$CH$_2$OH, —HNCO$_2$C$_2$H$_5$, —NHOH, —NHCONHOH and —NHCH$_3$; R$^1$ and R$^2$ are individually selected from the group consisting of

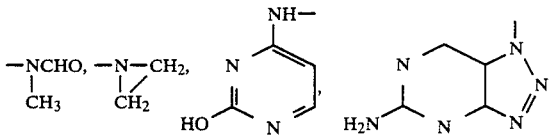

NHCH$_2$CH$_2$Cl, —NHCONHOH, —NHCO$_2$C$_2$H$_5$, 6-mercapropurin, 5-fluoruracil and prenissolin, R$^3$ is selected from the group consisting of hydrogen, —COCHR$_2^4$, —SO$_2$CH$_3$, —COC$_2$H$_5$, —CH$_2$CH$_2$R$_4$ and —CONH$_2$ and R$^4$ is the same as defined hereinabove or their salts.

* * * * *

UNITED STATES PATENT AND TRADEMARK OFFICE
CERTIFICATE OF CORRECTION

PATENT NO. : 4,956,457
DATED : Sept. 11, 1990
INVENTOR(S) : TAKEO TAKAYANAGI

It is certified that error appears in the above-identified patent and that said Letters Patent is hereby corrected as shown below:

Col.    Line

Claim 1   14      "$-CH_2C-H_2-OH$"   should be -- $-CH_2CH_2-OH$ --

Claim 2   14      " " " " " " " " " " " " " " " "

Signed and Sealed this

Seventh Day of January, 1992

Attest:

HARRY F. MANBECK, JR.

Attesting Officer      Commissioner of Patents and Trademarks